(12) United States Patent
Ancerewicz (10) Patent No.: US 11,471,587 B2
(45) Date of Patent: Oct. 18, 2022

(54) ORIFICE IRRIGATION DEVICE

(71) Applicant: Sigmund Ancerewicz, Cornelius, NC (US)

(72) Inventor: Sigmund Ancerewicz, Cornelius, NC (US)

(73) Assignee: Sigmund Ancerewicz, Cornelius, NC (US)

( * ) Notice: Subject to any disclaimer, the term of this patent is extended or adjusted under 35 U.S.C. 154(b) by 0 days.

(21) Appl. No.: 17/549,044

(22) Filed: Dec. 13, 2021

(65) Prior Publication Data

US 2022/0184296 A1 Jun. 16, 2022

Related U.S. Application Data

(60) Provisional application No. 63/125,049, filed on Dec. 14, 2020.

(51) Int. Cl.
*A61M 3/02* (2006.01)
*A61F 11/00* (2022.01)

(52) U.S. Cl.
CPC ......... *A61M 3/0279* (2013.01); *A61F 11/006* (2013.01); *A61M 3/027* (2013.01); *A61M 3/0287* (2013.01); *A61M 2210/0662* (2013.01)

(58) Field of Classification Search
CPC .. A61M 3/0279; A61M 3/027; A61M 3/0287; A61M 2210/0662; A61F 11/006
USPC ........................................ 604/93.01
See application file for complete search history.

(56) References Cited

U.S. PATENT DOCUMENTS 6,706,023 B1 * 3/2004 Huttner ............... A61M 3/0283
604/264

* cited by examiner

*Primary Examiner* — Phillip A Gray
(74) *Attorney, Agent, or Firm* — Shumaker, Loop & Kendrick, LLP (57) ABSTRACT

An orifice irrigation device includes a tubular component having a distal end and a proximal end and at least one bore axially extending from the proximal end to the distal end, the bore terminating at a plurality of orifices which extend at an angle from the bore; one or more flared wings coaxially positioned with respect to the tubular component, the at least one flared wing having a rim at its distal end; and one or more open flushing channels defined by the one or more flared wings, the flushing channels being defined by the side edges of the one or more flared wings.

14 Claims, 9 Drawing Sheets

ORIFICE IRRIGATION DEVICE

CROSS-REFERENCE TO RELATED APPLICATIONS

This application is a non-provisional application tracing priority and claiming benefit to U.S. Provisional Application No. 63/125,049, filed Dec. 14, 2020, entitled "ORIFICE IRRIGATION DEVICE", the entirety of which is expressly incorporated herein by reference.

TECHNICAL FIELD AND BACKGROUND OF THE INVENTION

This application relates to a bodily orifice irrigation device for use with a pressurized irrigating fluid to remove material from a bodily orifice such as the ear.

U.S. Pat. No. 6,706,023 to Huttner et al., assigned to Bionix Development Corporation of Toledo, Ohio, filed Dec. 3, 1999 and issued Mar. 16, 2004 (the "'023 patent") is directed to a DEVICE FOR IRRIGATION OF A BLIND ORIFICE. The '023 patent device has a tubular member with a bore axially extending from a proximal to a distal end with a number of orifices that extend at an angle from the bore. The irrigating fluid is directed through the bore and away from a central axis of the device through the orifices at the distal end. The tubular member may include an internal baffle that directs the fluid toward the orifices. The device may also include a flared member coaxially positioned with respect to the tubular member and defines a tip in close proximity to the distal end of the tubular member and a base which is in a spaced apart relationship from the tip. The flared member defines at least one passageway which defines at least one open channel adjacent the tip of the flared member and at least one enclosed channel adjacent the base of the flared member. The enclosed channels are defined by the sides and the base of the flared member. The open channel is contiguous to the enclosed channel. Notably, in the '023 patent device, the circumference of the base of the flared member is unbroken and/or continuous, which disadvantageously inhibits inward deformation of at least a portion of the circumference of the flared member and/or causes non-ergonomical circumferential bulging of the flared member during insertion and/or while inserted in the bodily orifice leading to both discomfort and unsatisfactory fitting within the orifice while in use.

SUMMARY

The above and other needs are met by embodiments of the present invention, which are directed to an irrigation device having a tubular component with a bore axially extending from a proximal end to a distal end and terminating at a plurality of orifices, which extend at an angle from the bore. The irrigation device has flared wings coaxially positioned with respect to the tubular component and have rims at their distal ends and also have flushing channels defined by side edges of the flared wings. In some embodiments, where the irrigation device includes multiple flared wings, for example, three circumferentially equidistant flared wings, the flared wings can axially, inwardly deform in concert with one another and without a bulging circumferential rim during insertion and when the device is inserted into the orifice resulting in a better and more comfortable fit within, for example, a patient while in use.

According to some embodiments, the irrigation device also includes one or more anchors coupled to (i) the one or more flared wings and (ii) the tubular component. In some such embodiments, each wing comprises a first flap and a second flap, the first flap and the second flap disposed on opposite sides of the anchor coupled with the wing. In some of these embodiments, each first flap and second flap comprises a corner, each first flap and second flap configured to flex so that the corners move from the unflexed position toward the tubular component. In some such embodiments, at least partially because of the coupled anchors and the concave shape, each first flap and second flap is configured to resist flexing from the unflexed position so that the corners move away from the bore into a convex shape.

According to some embodiments, the one or more flared wings comprise an initial flaring point located along the circumference of the outer surface of the tubular component where the outer surface begins to flare at a flaring angle to an axis of the tubular component to create the one or more wings, a flaring reversal point located along the circumference of the outer surface of the tubular component where the outer surface flaring begins to reverse and the flaring angle reaching a maximum, and a flaring constant point located along the circumference of the outer surface of the tubular component where the flaring angle remains constant until termination of the one or more wings.

In some embodiments, the one or more open flushing channels comprise an intake formed by portions of the one or more wings proximate the tubular component and an exit formed by portions of the one or more wings distal the tubular component.

In some embodiments, the irrigation device also includes a center aperture disposed among the radial apertures, the center aperture at the distal end of the bore.

In some embodiments, each of the one or more wings comprises scalloping at its distal edge.

According to embodiments of the invention, a bodily orifice irrigation device includes a tubular component having a distal end and a proximal end and a bore axially extending from the proximal end to the distal end, the bore terminating at a plurality of orifices which extend at an angle from the bore; a first flared wing coaxially positioned with respect to the tubular component, the first flared wing having first and second side edges and a rim at its distal end; a second flared wing coaxially positioned with respect to the tubular component, the second flared wing having first and second side edges and a rim at its distal end; a first open flushing channel defined by the first side edge of the first flared wing and the first side edge of the second flared wing; a third flared wing coaxially positioned with respect to the tubular component, the third flared wing having first and second side edges and a rim at its distal end; a second open flushing channel defined by the second side edge of the first flared wing and the first side edge of the third flared wing; and a third open flushing channel defined by the second side edge of the third flared wing and the second side edge of the first flared wing. In certain aspects, the rims of each flared wing forms a discontinuous circumference. The rims of the flared wings are advantageously configured to each resiliently deform inwardly, for example in a concerted movement, in a direction towards the tubular component during insertion and while inserted in the bodily orifice thereby minimizing and/or eliminating discomfort and while concurrently achieving a satisfactory fitting within the orifice while in use In some embodiments, the bodily orifice irrigation device also includes a first anchor coupled to (i) the first flared wing and (ii) the tubular component; a second anchor coupled to (i) the second flared wing and (ii) the tubular component; and a third anchor coupled to (i) the third flared wing and (ii) the tubular component.

In some such embodiments, the first flared wing comprises a first flap and a second flap disposed on opposite sides of the first anchor coupled to the first flared wing; the second flared wing comprises a first flap and a second flap disposed on opposite sides of the second anchor coupled to the second flared wing; and the third flared wing comprises a first flap and a second flap disposed on opposite sides of the third anchor coupled to the third flared wing.

In some such embodiments, each first flap and second flap are configured to rest in an unflexed position having a generally concave shape, and wherein each first flap and second flap comprises a corner, each first flap and second flap configured to flex so that the corners move from the unflexed position toward the tubular component.

In some such embodiments, each first flap and second flap are configured to, at least partially because of the coupled anchors and the concave shape, to resist flexing the corners from the unflexed position away from the bore into a convex shape.

In some embodiments, the first flared wing, the second flared wing, and the third flared wing each comprise an initial flaring point located along the circumference of the outer surface of the tubular component where the outer surface begins to flare at a flaring angle to an axis of the tubular component to create the wings, a flaring reversal point located along the circumference of the outer surface of the tubular component where the outer surface flaring begins to reverse and the flaring angle reaching a maximum, and a flaring constant point located along the circumference of the outer surface of the tubular component where the flaring angle remains constant until termination of the wings.

In some embodiments, the one or more open flushing channels comprise an intake formed by portions of the one or more wings proximate the tubular component and an exit formed by portions of the one or more wings distal the tubular component.

In some embodiments, the bodily orifice irrigation device also includes a center aperture disposed among the radial apertures, the center aperture at the distal end of the bore.

In some embodiments, each of the wings comprises scalloping at its distal edge.

According to embodiments of the invention, a method for ear irrigation using an ear irrigation device for irrigation of an ear of a user includes (a) a tubular component having a distal end and a proximal end and at least one bore axially extending from the proximal end to the distal end, the bore terminating at a plurality of orifices which extend at an angle from the bore; (b) one or more flared wings coaxially positioned with respect to the tubular component, the at least one flared wing having a rim at its distal end; and (c) one or more open flushing channels defined by the one or more flared wings, the flushing channels being defined by the side edges of the one or more flared wings; wherein the method comprises: (i) receiving, using the ear irrigation device, fluid from a fluid source; (ii) expelling, using the ear irrigation device, the fluid from the proximal end of the tubular component via the plurality of orifices extending from an angle from the bore into the ear of the user; and (iii) flushing, using the ear irrigation device, the fluid from the ear of the user via the one or more open flushing channels defined by the one or more flared wings.

In some embodiments, the method also includes providing the ear irrigation device for use irrigating the ear of the user.

DETAILED DESCRIPTION OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout. Referring now to the drawings and the listing of machine components set out below, the invention according to a preferred embodiment is described in further detail.

Referring to FIGS. 1-9, an orifice irrigation device 100 according to embodiments of the invention is illustrated. The irrigation device 100 has a distal end 102 and a proximal end 104. The irrigation device 100 defines a tubular component 106 that defines a longitudinal opening or bore 108 that extends from the proximal end 104 to the distal end 102 of the irrigation device 100 such that the proximal and distal ends are in fluid communication with one another.

Figure 9:
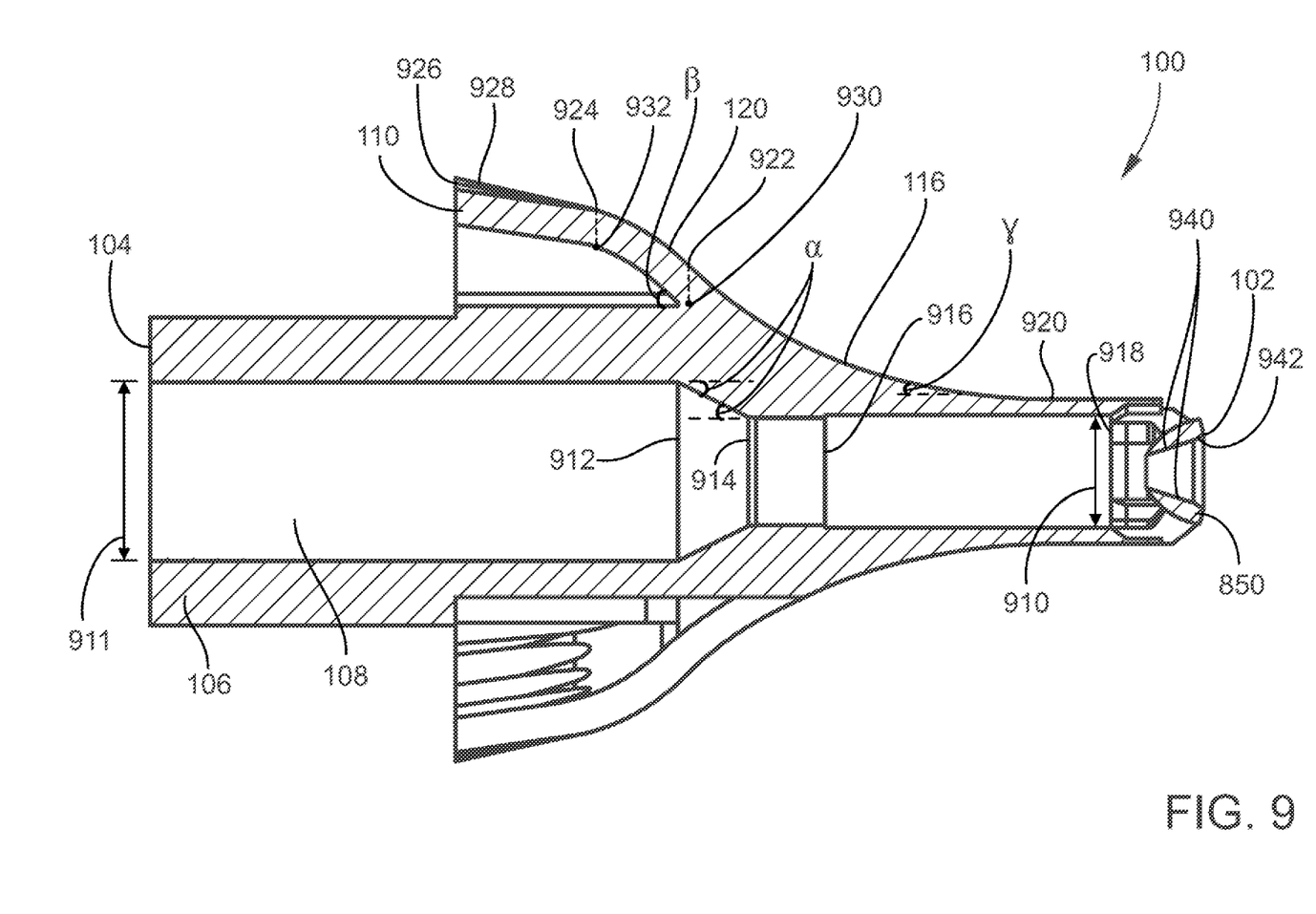
FIG. 9 illustrates a cross-sectional view along lines 9-9 of FIG. 7 of the orifice irrigation device.

As shown in FIG. 9, the bore 108 has an internal diameter 911 adjacent the proximal end 104 that is greater than its internal diameter 910 adjacent the distal end 102. In other embodiments, the internal diameter of the bore 106 may gradually decrease from proximal end 104 to distal end 102 or in yet other embodiments may decrease in one or more sections from proximal-to-distal, such as the section of the bore 106 from location 912 to location 914 where the bore 106 is tapered at an angle $\alpha$, and in other sections the internal diameter may be consistent, such as the section of the bore 106 from location 914 to location 916 or the section from location 916 to location 918.

Figure 1:
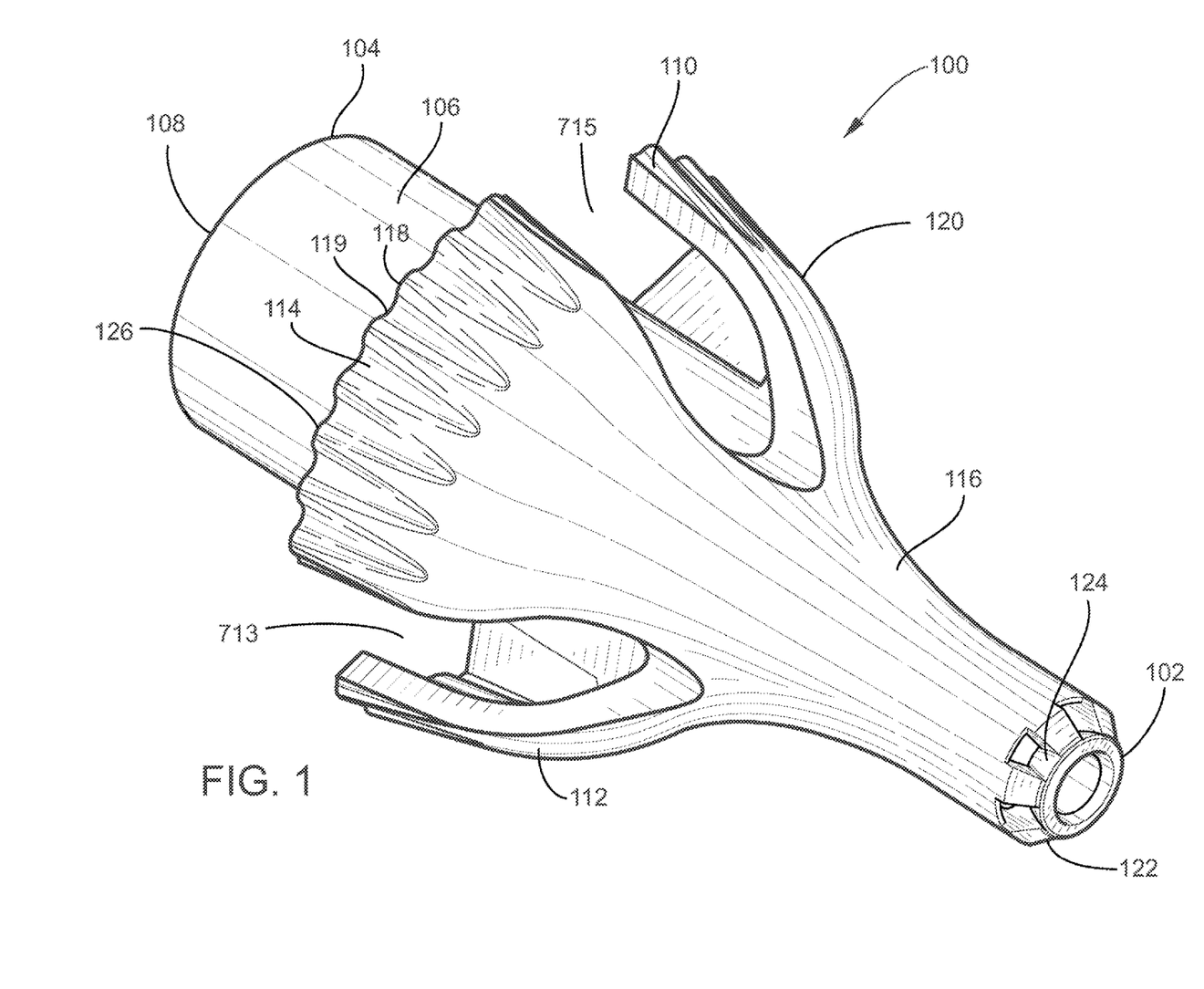
FIG. 1 illustrates a perspective view of an orifice irrigation device according to embodiments of the invention.
Figure 2:
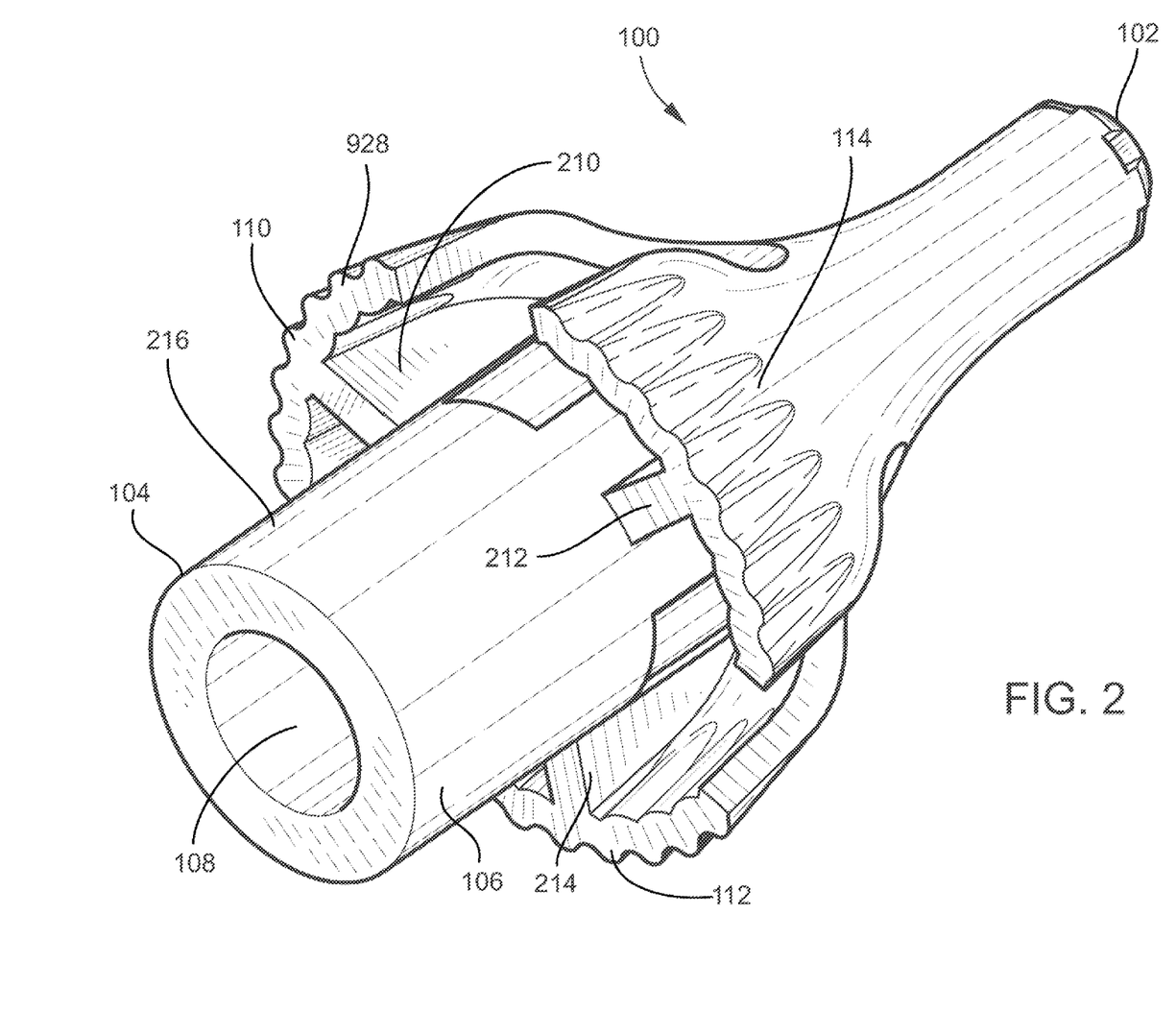
FIG. 2 illustrates a second perspective view of the orifice irrigation device of FIG. 1.

Referring to FIGS. 1, 2, and 9 collectively, the irrigation device 100 has a plurality of wings 110, 112, and 114. In the embodiment shown there are three (3) wings 110, 112, and 114, but in other embodiments, there may be two wings, four wings, or more wings. In the embodiment shown and some other embodiments, the wings 110, 112, and 114 are evenly circumferentially spaced around the tubular component 106. In other embodiments, the wings may be unevenly spaced around the tubular component 106. Each of the wings 110, 112, and 114, in the embodiment shown, are integrally connected with the tubular component 106 and flare coaxially from the tubular component 106 and terminate at a partially-circumferential rim 126 (or a discontinuous circumference formed from by each wing that are not connected to one another by their respective rims). The rims of the flared wings are advantageously configured to each resiliently deform inwardly, for example in a concerted movement, in a direction towards the tubular component during insertion and while inserted in the bodily orifice thereby minimizing and/or eliminating discomfort and while concurrently achieving a satisfactory fitting within the orifice while in use.

The tubular component 106 has an outer surface 116 that is, at its distal end, parallel with the longitudinal axis of the tubular component 106. The outer surface 116 begins to flare axially outwardly from distal to proximal at initial flaring point 920. The angle that the distal outer surface 116 flares with respect to the longitudinal axis of the tubular component is represented in FIG. 9 by the angle γ. Angle γ increases from the initial flaring point until the flaring reversal point 922 is reached, at which point, the angle γ begins to reduce moving toward the flaring constant point 924, at which point, the angle γ remains constant until the distal end of wing 110. The constant angle γ between the flaring constant point 924 and the distal end 926 does not account for the scalloped end 928 of wing 110, but rather refers to the mean angle of flare remaining constant from the flaring constant point 924 to the distal end 926 or rim 126. In other words, in a trough 119 of the scalloped end 928, angle γ may be less than at flaring constant point 924, and in a peak 118 of the scalloped end 928, angle γ may be greater than at flaring constant point 924. However, in the shown embodiment, the mean angle γ at the distal end 926 of the wing 110 is consistent with the angle γ at the flaring constant point 924.

When the irrigation device is being inserted into the orifice or when it has been inserted into the orifice, the wings inwardly deform in concert according to the anatomical geometry of the orifice. The troughs 119 of the scalloped ends 928 of the inwardly deformed wings rest against the internal walls of the orifice, and the peaks 118 opposite the troughs 119 ensure no air-tight seal is created between the rims of the wings and the internal surface of the orifice. The multiple small channels between the scalloped ends 928 and the internal surface of the orifice enables flushing of fluid and debris from the orifice in concert with the flushing channels 711, 713, and 715 discussed below with reference to FIG. 7.

Angle β is related to angle γ in the shown embodiment as the two are the same at the same longitudinal location. More specifically, the flaring reversal point 922 is at the same location along the longitudinal axis of the tubular component as wing initiation point 930, and at this shared longitudinal location, angles γ and β are equal. Similarly, flaring constant point 924 is longitudinally parallel with internal flaring constant point 932, at which longitudinal point, angles γ and β are equal and constant until the distal end 926.

As noted above, the wings 110, 112, and 114 are integral with the tubular component in the shown embodiment, but for ease of discussion purposes, the outer surface 120 of wing 110 is described distinctly from outer surface 920 of the tubular component; however, the outer surface 116 and outer surface 120 are contiguous. The transition between outer surface 116 and outer surface 120 is at the flaring reversal point 922.

Referring to FIG. 2, each of wings 110, 112, and 114 have an anchor 210, 212, and 214, respectively. The anchors 210, 212, and 214 connect the wings 110, 112, and 114 to the outer surface 216 of the tubular component 106. In other embodiments, wings 110, 112, and 114 do not have corresponding anchors. The anchors 210, 212, and 214 inhibit the wings 110, 112, and 114, which are typically deformable, from bending too far backward and away from the outer surface 216 of the tubular component 106.

Figure 8:
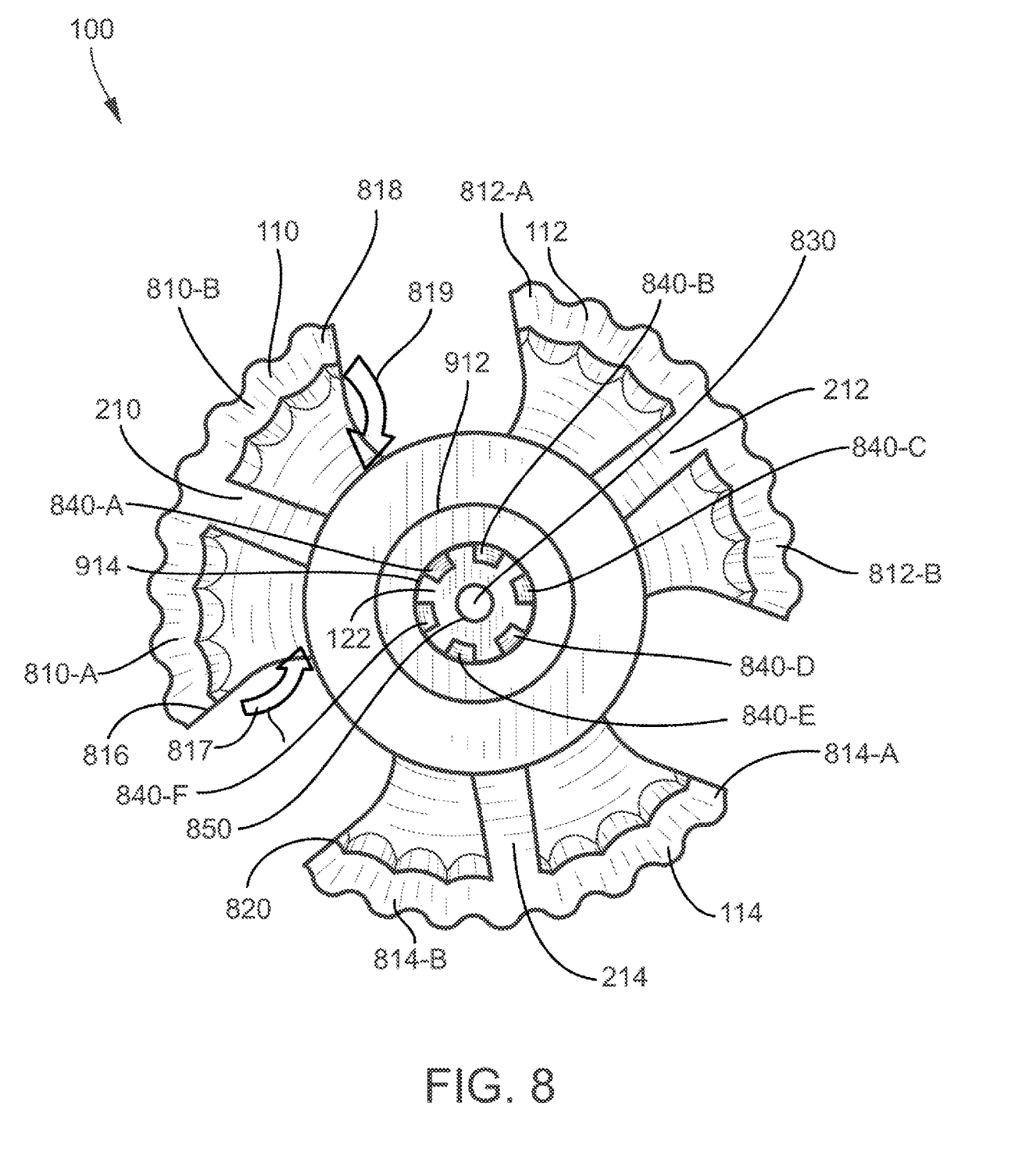
FIG. 8 illustrates a bottom view of the orifice irrigation device of FIG. 1.

Referring to FIG. 8, which is a bottom view of the irrigation device 100, the wings 110, 112, and 114, each have a first flap 810-A, 812-A, and 814-A and a second flap 810-B, 812-B, and 814-B, respectively. Each of the first flaps 810-A, 812-A, and 814-A and second flaps 810-B, 812-B, and 814-B are typically deformable, and are enabled to fold inwardly axially to the tubular component from the positioning shown in the figures. The anchors 210, 212, and 214 tend to inhibit the wings 110, 112, and 114 from folding inwardly axially as entire wings, but the individual flaps, as discussed, are free to fold inwardly axially, and return to their initial staring positions depicted in the figures. Arrow 817 indicates the direction in which the corner 816 of flap 810-A is configured to fold. Arrow 819 indicates the direction in which the corner 818 of flap 810-B is configured to fold. In the event corners 816 and/or 818 fold inwardly as shown, they tend to return to their initial positioning as shown in the figures. Notably, from the perspective of FIG. 8, the underside of the wings 110, 112, and 114 are relatively bowed to inhibit bending of the wings outwardly axially, which bending is further inhibited by the anchors.

Importantly, were corner 816 of wing 110 and corner 820 of wing 114 tied together, such as by being part of an unbroken continuous circumference of a single wing or so-called flared member, then the flaps, wings, or so-called flared member would be significantly inhibited from deformation such as folding inwardly axially as described above with respect to the presently disclosed embodiments. Such inhibition of deformation tends to prevent beneficial release of fluid and debris and conformance to anatomy in a bodily orifice.

Figure 7:
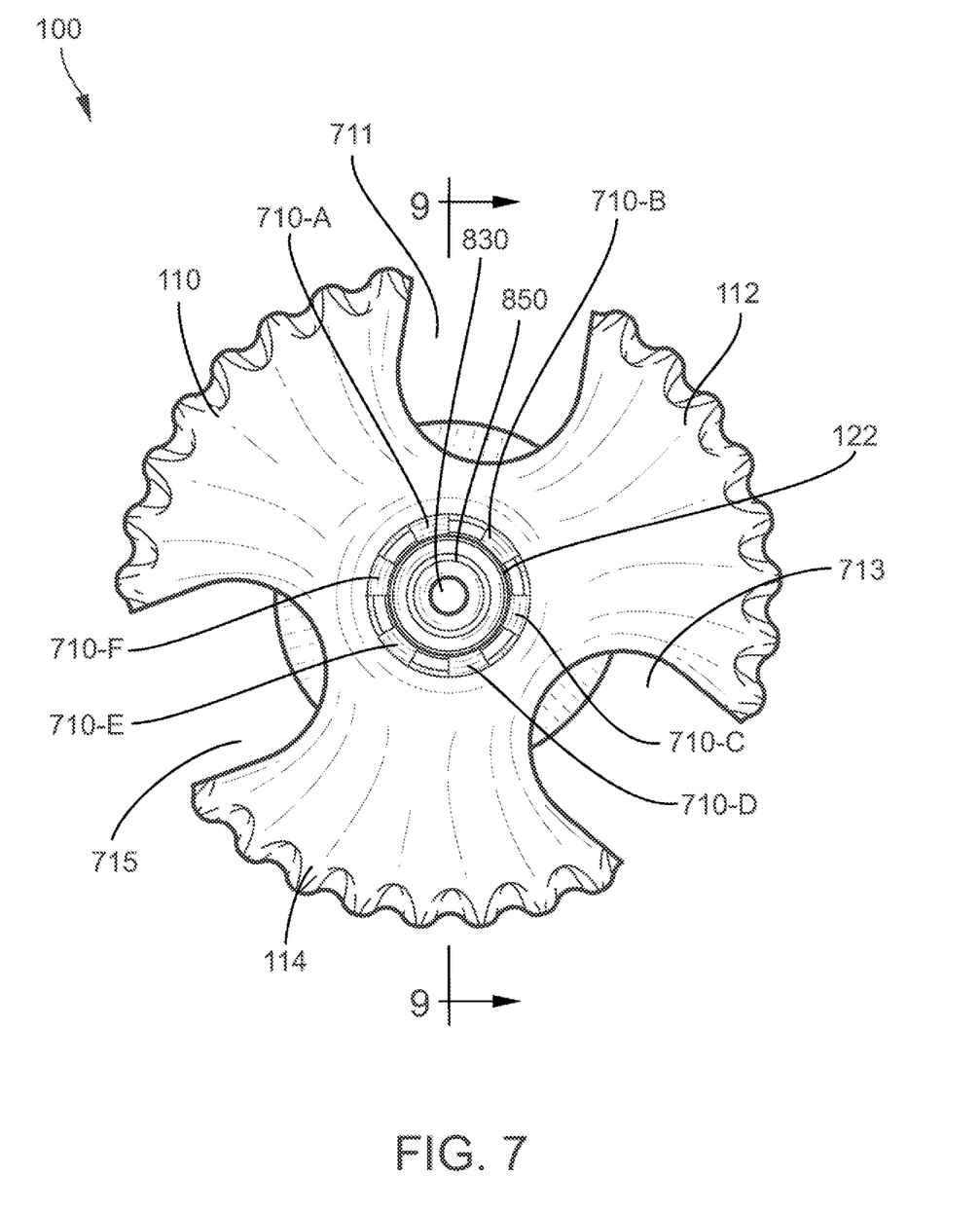
FIG. 7 illustrates a top view of the orifice irrigation device of FIG. 1.

The underside of the nozzle assembly 122 is shown in FIG. 8, and the overhead of the nozzle assembly 122 is shown in FIG. 7. Referring to both FIGS. 7 and 8 concurrently, the nozzle assembly 122 includes a nozzle 850 that defines a center aperture 830 and a plurality of nozzle spokes 710-A, 710-B, 710-C, 710-D, 710-E, and 710-F that together define a plurality of radial apertures 840-A, 840-B, 840-C, 840-D, 840-E, and 840-F. In some embodiments like the shown embodiment, the nozzle spokes are contiguous with the tubular component 106, but in others, the nozzle spokes 710-A, 710-B, 710-C, 710-D, 710-E, and 710-F are distinct components connected to the tubular component 106.

The nozzle 850 is connected to each of the nozzle spokes 710-A, 710-B, 710-C, 710-D, 710-E, and 710-F in order to form the radial apertures 840-A, 840-B, 840-C, 840-D, 840-E, and 840-F. As shown in FIG. 9, the nozzle 850 may include a tapered inner surface having a smaller diameter proximally, i.e., at the intake of the nozzle 850 and a greater diameter distally, i.e., at the exit of the nozzle. In some embodiments, such as the embodiment shown in the figures, the nozzle 850 has an intake inner surface 940 tapered at a relatively smaller angle compared to the exit inner surface 942, which is tapered at a relatively greater angle. The external surface 124 of the nozzle 850 as shown in FIG. 1, may be curved in a concave manner from the perspective of the radial apertures 840-A, 840-B, 840-C, 840-D, 840-E, and 840-F.

Figure 3:
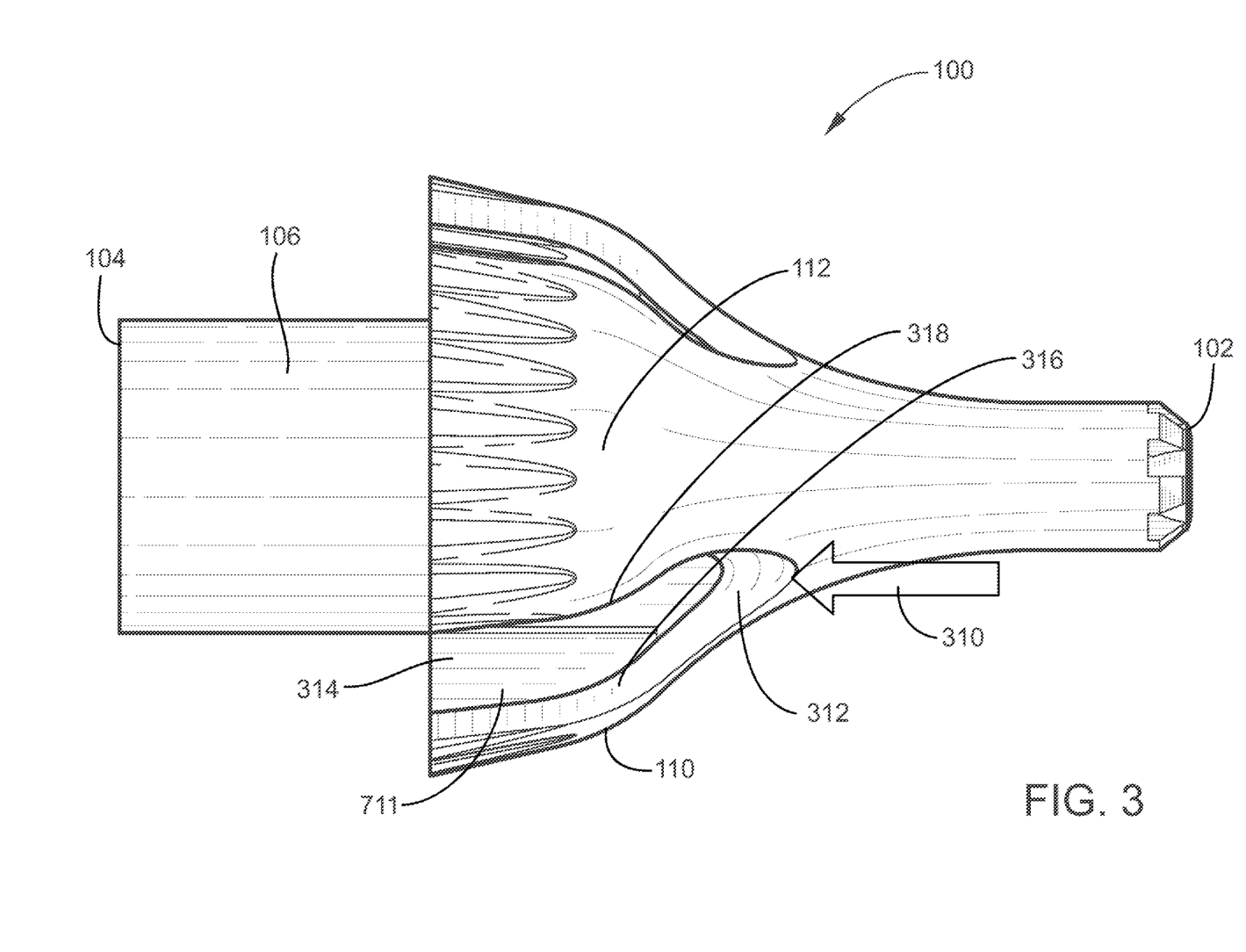
FIG. 3 illustrates a first side view of the orifice irrigation device of FIG. 1.
Figure 4:
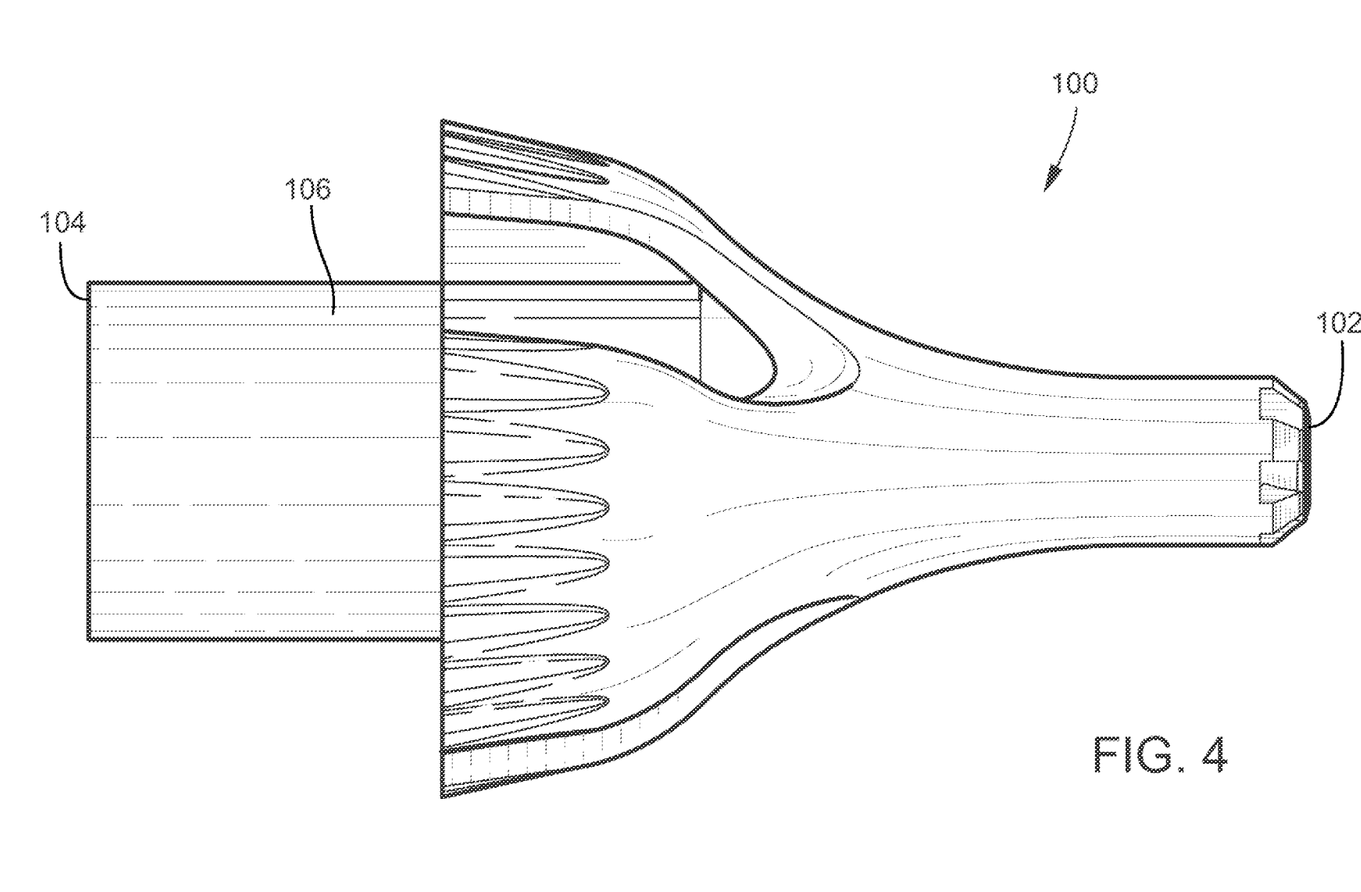
FIG. 4 illustrates a second side view of the orifice irrigation device of FIG. 1.
Figure 5:
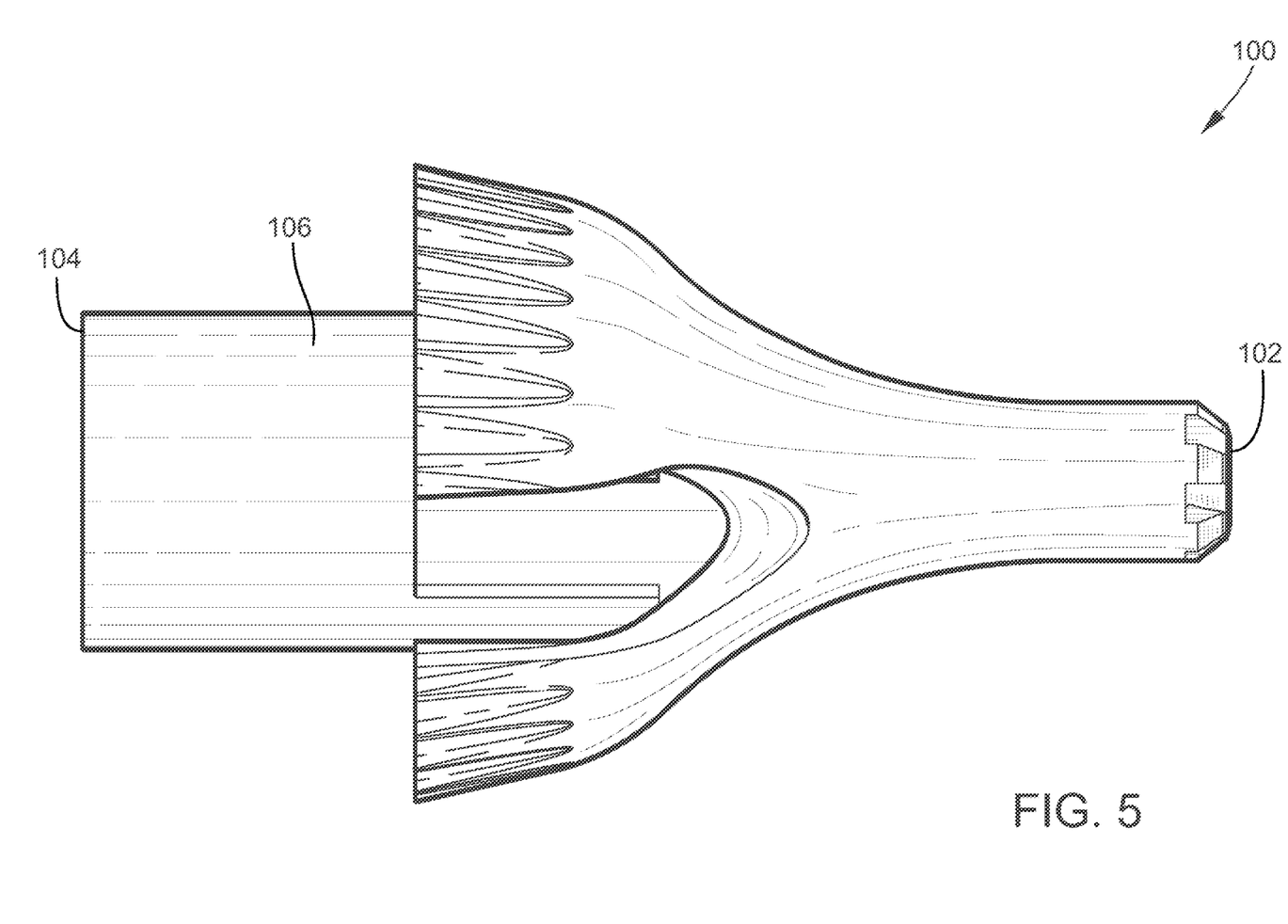
FIG. 5 illustrates a third side view of the orifice irrigation device of FIG. 1.
Figure 6:
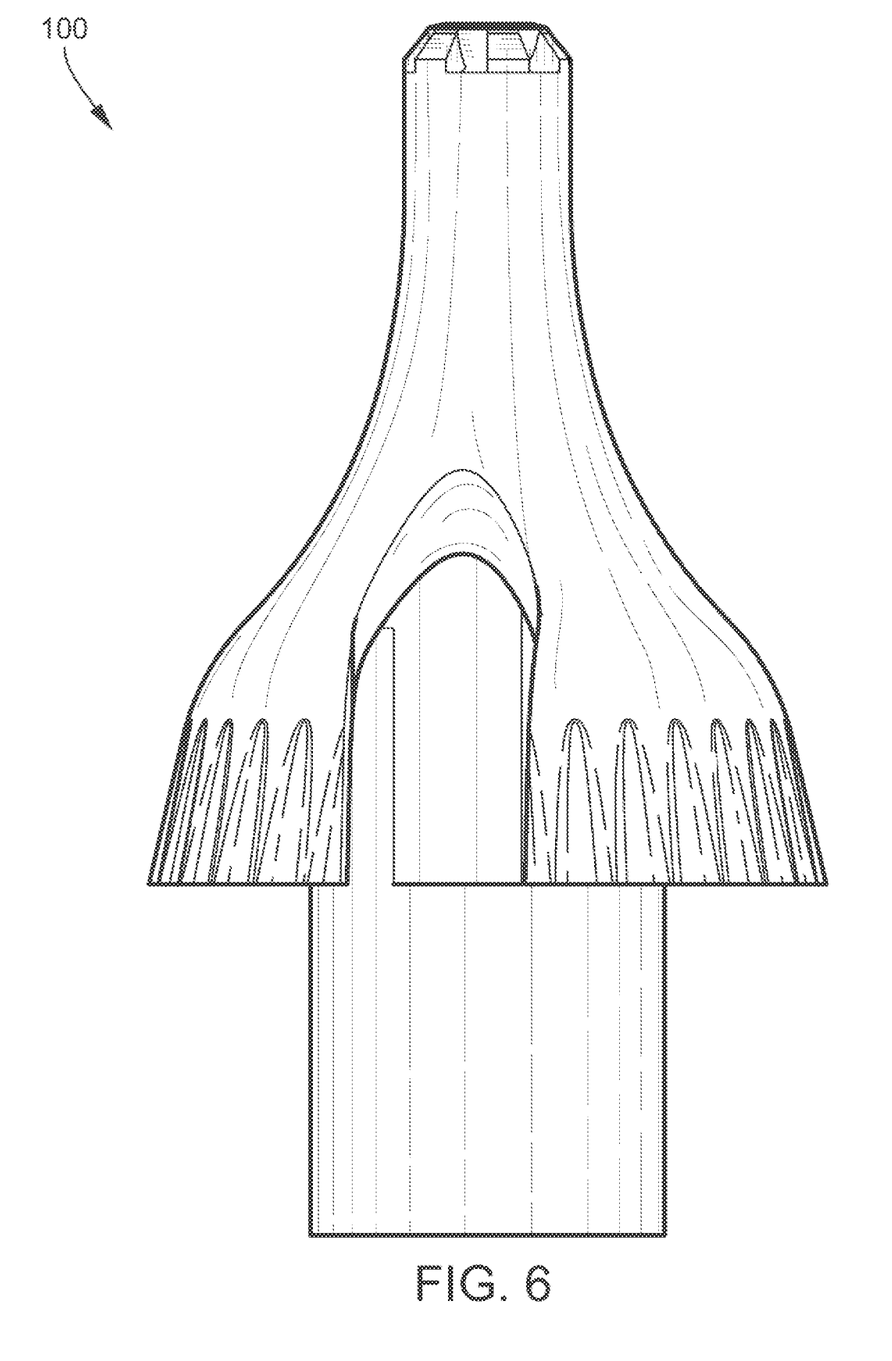
FIG. 6 illustrates a fourth side view of the orifice irrigation device of FIG. 1.

Referring now to FIG. 7, the wings 110, 112, and 114 together with the tubular component 106 form flushing channels 711, 713, and 715. The flushing channels are not fully enclosed, or in other words, the flushing channels do not have a fully circumferential rim or base of a flared member defining them. Rather, the flushing channels are configured to enable maximum flush of waste fluid and debris without inhibition by a fully-enclosed rim or base. Referring to FIG. 3, waste fluid and debris is exiting the orifice in the direction of arrow 310. The waste fluid and debris is received in the flushing channel 711 at its intake 312 and expelled through its exit 314. Side edge 316 of wing 110 and side edge 318 of wing 112 together form the flushing channel 711. The exit 314 is an open exit, meaning that the exit 314 is not closed-off by a circumferential edge of the wings or a so-called rim or base of a singular flared member. As shown in the top view of FIG. 7, the flushing channels 711, 713, and 715 appear as close to U-shaped open channels. The waste fluid and debris travels into the page of FIG. 7, i.e., in the direction of arrow 310 of FIG. 3. The U-shaped flushing channels as seen in FIG. 7, provide a maximized opportunity to flush waste. Such an open exit provides the benefit of flushing a greater volume of waste fluid and debris in a given period, or stated another way, the open exit of the flushing channels 711, 713, and 715 ensures no pressure build-up within the bodily orifice due to the influx of fluid from the nozzle assembly, because the waste fluid and debris can freely exit through the open exits 314 of the flushing channels 711, 713, and 715.

As described herein, an irrigation device has been described with reference to specific embodiments and examples. Various details of the invention may be changed without departing from the scope of the invention. Furthermore, the foregoing description of the preferred embodiments of the invention and best mode for practicing the invention are provided for the purpose of illustration only and not for the purpose of limitation, the invention being defined by the claims.

It is understood that the systems and devices described herein illustrate one embodiment of the invention. It is further understood that one or more of the systems, devices, or the like can be combined or separated in other embodiments and still function in the same or similar way as the embodiments described herein.

While certain exemplary embodiments have been described and shown in the accompanying drawings, it is to be understood that such embodiments are merely illustrative of, and not restrictive on, the broad invention, and that this invention not be limited to the specific constructions and arrangements shown a and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the invention. Therefore, it is to be understood that, within the scope of the appended claims, the invention may be practiced other than as specifically described in this application.

I claim:

1. An irrigation device comprising:
   (a) a tubular component having a distal end and a proximal end and at least one bore axially extending from the proximal end to the distal end, the bore terminating at a plurality of radial apertures each extending at an angle from the bore;
   (b) one or more flared wings coaxially positioned with respect to the tubular component, the at least one flared wing having a rim at its distal end;
   (c) one or more open flushing channels defined by the one or more flared wings, the flushing channels being defined by the side edges of the one or more flared wings; and
   (d) one or more anchors coupled to (i) the one or more flared wings and (ii) the tubular component, wherein each wing comprises a first flap and a second flap, the first flap and the second flap disposed on opposite sides of the anchor coupled with the wing and each first flap and second flap comprises a corner, each first flap and second flap configured to flex so that the corners move from the unflexed position toward the tubular component.

2. The irrigation device of claim 1, wherein, at least partially because of the coupled anchors and the concave shape, each first flap and second flap is configured to resist flexing from the unflexed position so that the corners move away from the bore into a convex shape.

3. The irrigation device of claim 1, wherein the one or more flared wings comprise an initial flaring point located along the circumference of the outer surface of the tubular component where the outer surface begins to flare at a flaring angle to an axis of the tubular component to create the one or more wings, a flaring reversal point located along the circumference of the outer surface of the tubular component where the outer surface flaring begins to reverse and the flaring angle reaching a maximum, and a flaring constant point located along the circumference of the outer surface of the tubular component where the flaring angle remains constant until termination of the one or more wings.

4. The irrigation device of claim 1, wherein the one or more open flushing channels comprise an intake formed by portions of the one or more wings proximate the tubular component and an exit formed by portions of the one or more wings distal the tubular component.

5. The irrigation device of claim 1, further comprising a center aperture disposed among the radial apertures, the center aperture at the distal end of the bore.

6. The irrigation device of claim 1, wherein each of the one or more wings comprises scalloping at its distal edge.

7. A bodily orifice irrigation device comprising:
   (a) a tubular component having a distal end and a proximal end and a bore axially extending from the proximal end to the distal end, the bore terminating at a plurality of orifices which extend at an angle from the bore;
   (b) a first flared wing coaxially positioned with respect to the tubular component, the first flared wing having first and second side edges and a rim at its distal end;
   (c) a second flared wing coaxially positioned with respect to the tubular component, the second flared wing having first and second side edges and a rim at its distal end; and
   (d) a first open flushing channel defined by the first side edge of the first flared wing and the first side edge of the second flared wing;
   (e) a third flared wing coaxially positioned with respect to the tubular component, the third flared wing having first and second side edges and a rim at its distal end;
   (f) a second open flushing channel defined by the second side edge of the first flared wing and the first side edge of the third flared wing;
   (g) a third open flushing channel defined by the second side edge of the third flared wing and the second side edge of the first flared wing;
   (h) a first anchor coupled to (i) the first flared wing and (ii) the tubular component;

(i) a second anchor coupled to (i) the second flared wing and (ii) the tubular component; and (j) a third anchor coupled to (i) the third flared wing and (ii) the tubular component, wherein the first flared wing comprises a first flap and a second flap disposed on opposite sides of the first anchor coupled to the first flared wing; the second flared wing comprises a first flap and a second flap disposed on opposite sides of the second anchor coupled to the second flared wing; and the third flared wing comprises a first flap and a second flap disposed on opposite sides of the third anchor coupled to the third flared wing and each first flap and second flap are configured to rest in an unflexed position having a generally concave shape, and wherein each first flap and second flap comprises a corner, each first flap and second flap configured to flex so that the corners move from the unflexed position toward the tubular component.

8. The bodily orifice irrigation device of claim 7, wherein each first flap and second flap are configured to, at least partially because of the coupled anchors and the concave shape, to resist flexing the corners from the unflexed position away from the bore into a convex shape.

9. The bodily orifice irrigation device of claim 7, wherein the first flared wing, the second flared wing, and the third flared wing each comprise an initial flaring point located along the circumference of the outer surface of the tubular component where the outer surface begins to flare at a flaring angle to an axis of the tubular component to create the wings, a flaring reversal point located along the circumference of the outer surface of the tubular component where the outer surface flaring begins to reverse and the flaring angle reaching a maximum, and a flaring constant point located along the circumference of the outer surface of the tubular component where the flaring angle remains constant until termination of the wings.

10. The bodily orifice irrigation device of claim 7, wherein the one or more open flushing channels comprise an intake formed by portions of the one or more wings proximate the tubular component and an exit formed by portions of the one or more wings distal the tubular component.

11. The bodily orifice irrigation device of claim 7, further comprising a center aperture disposed among the radial apertures, the center aperture at the distal end of the bore.

12. The bodily orifice irrigation device of claim 7, wherein each of the wings comprises scalloping at its distal edge.

13. A method for ear irrigation using an ear irrigation device of claim 1 for irrigation of an ear of a user, the ear irrigation device comprising:
(a)
(b)
(i) receiving, while using the ear irrigation device, fluid from a fluid source;
(ii) expelling, while using the ear irrigation device, the fluid from the proximal end of the tubular component via the plurality of orifices extending from an angle from the bore into the ear of the user; and
(iii) flushing, while using the ear irrigation device, the fluid from the ear of the user via the one or more open flushing channels defined by the one or more flared wings.

14. The method of claim 13, further comprising irrigating the ear of the user.

* * * * *